(12) United States Patent
Kheradvar et al.

(10) Patent No.: US 11,730,593 B2
(45) Date of Patent: Aug. 22, 2023

(54) PERCUTANEOUS HEART VALVE DELIVERY AND IMPLANTATION SYSTEM ENABLING FRACTURE OF A PREVIOUSLY PRESENT VALVE

(71) Applicant: THE REGENTS OF THE UNIVERSITY OF CALIFORNIA, Oakland, CA (US)

(72) Inventors: Arash Kheradvar, Irvine, CA (US); Gregory S. Kelley, Santee, CA (US); Mohammad Sarraf, Birmingham, AL (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 275 days.

(21) Appl. No.: 16/989,052

(22) Filed: Aug. 10, 2020

(65) Prior Publication Data

US 2021/0045872 A1 Feb. 18, 2021

Related U.S. Application Data

(60) Provisional application No. 62/885,999, filed on Aug. 13, 2019.

(51) Int. Cl.
*A61F 2/24* (2006.01)
*A61F 2/95* (2013.01)
(Continued)

(52) U.S. Cl.
CPC .............. *A61F 2/2433* (2013.01); *A61B 8/12* (2013.01); *A61B 90/37* (2016.02); *A61F 2/2418* (2013.01);
(Continued)

(58) Field of Classification Search
CPC .... A61F 2/2433; A61F 2/2418; A61F 2/9522; A61F 2250/0048; A61B 8/12; A61B 90/37; A61B 2017/00783; A61B 2090/378
(Continued)

(56) References Cited

U.S. PATENT DOCUMENTS 8,133,270 B2 3/2012 Kheradvar et al.
10,835,713 B2 * 11/2020 Homsy ............ A61M 25/0147
(Continued)

OTHER PUBLICATIONS

Sathananthan et al. ("Valve-in-vale Transcatheter Aortic Valve Replacement and Bioprosthetic valve fracture comparing different transcatheter heart valve designs") (Year: 2019).*
(Continued)

*Primary Examiner* — Suzette J Gherbi
(74) *Attorney, Agent, or Firm* — Nguyen Tarbet LLC (57) ABSTRACT

A percutaneous heart valve delivery system including a valve delivery catheter coupled with a first inflatable balloon positioned at a distal end of the valve delivery catheter, wherein the first inflatable balloon is configured to fracture a previously implanted prosthetic heart valve; and a replacement transcatheter heart valve positioned proximal to the first inflatable balloon, wherein the replacement transcatheter heart valve is configured to be implanted subsequently within the previously implanted, fractured prosthetic heart valve, following fracture of the previously implanted heart valve without withdrawal of the percutaneous heart valve delivery system. Also disclosed are methods of implantation of a new heart valve within a previously implanted prosthetic heart valve and methods of valvuloplasty of a native heart valve.

20 Claims, 9 Drawing Sheets

(51) Int. Cl.
*A61B 90/00* (2016.01)
*A61B 8/12* (2006.01)
*A61B 18/14* (2006.01)
*A61B 17/00* (2006.01)

(52) U.S. Cl.
CPC ........ *A61F 2/9522* (2020.05); *A61B 18/1492* (2013.01); *A61B 2017/00783* (2013.01); *A61B 2090/378* (2016.02); *A61F 2210/0014* (2013.01); *A61F 2250/0048* (2013.01)

(58) Field of Classification Search
USPC .................................................. 623/2.1–2.19
See application file for complete search history.

(56) References Cited

U.S. PATENT DOCUMENTS

| | | | | |
|---|---|---|---|---|
| 11,413,144 | B2* | 8/2022 | Rothstein | A61F 2/966 |
| 2007/0005131 | A1* | 1/2007 | Taylor | A61F 2/2433 |
| | | | | 623/2.11 |
| 2009/0281619 | A1* | 11/2009 | Le | A61M 25/0147 |
| | | | | 623/2.11 |
| 2012/0283820 | A1* | 11/2012 | Tseng | A61F 2/2418 |
| | | | | 623/1.23 |
| 2013/0030519 | A1* | 1/2013 | Tran | A61F 2/958 |
| | | | | 623/2.11 |
| 2014/0277414 | A1 | 9/2014 | Kheradvar | |
| 2019/0015203 | A1 | 1/2019 | Kheradvar | |
| 2019/0133764 | A1 | 5/2019 | Carr et al. | |
| 2019/0282360 | A1 | 9/2019 | Colavito et al. | |
| 2021/0275299 | A1* | 9/2021 | Peterson | A61F 2/2433 |
| 2022/0183830 | A1* | 6/2022 | Tseng | A61F 2/2418 |
| 2022/0233307 | A1* | 7/2022 | Tuval | A61F 2/2412 |

OTHER PUBLICATIONS

U.S. Appl. No. 16/866,913, filed May 5, 2020, Kheradvar et al.

Chhatriwalla, et al., 2017 "Bioprosthetic Valve Fracture Improves the Hemodynamic Results of Valve-in-Valve Transcatheter Aortic Valve Replacement," *Circ Cardiovasc Interv;*10:e005216 (in 6 pages).

Dasi, et al., 2017 "On The Mechanics of Transcatheter Aortic Valve Replacement," Ann Biomed Eng. 45(2): 310-331 (in 39 pages).

* cited by examiner

PERCUTANEOUS HEART VALVE DELIVERY AND IMPLANTATION SYSTEM ENABLING FRACTURE OF A PREVIOUSLY PRESENT VALVE

BACKGROUND OF THE INVENTION

Field

A percutaneous heart valve delivery system for delivery and implantation of a prosthetic valve, which incorporates means to fracture a previously-implanted prosthetic valve in situ without interfering with the transcatheter valve to be implanted.

Background

In many instances, patients with previously-implanted surgical prosthetic valve who require transcatheter valve-in-valve (VIV) replacement have higher residual pressure gradients, in which transcatheter valve implantation leads to unfavorable outcome due to patient-prosthetic mismatch, confirmed by further reduction of the valve area and non-optimal expansion of the new transcatheter valve. Recently, bioprosthetic valve fracture (BVF) is performed before the VIV transcatheter valve implantation procedure using an inflatable balloon. Balloon expansion to the point of fracturing the bioprosthetic sewing ring depends on the size and the specific bioprosthetic manufacturer (Chhatriwalla A K, et al. 2017 "Bioprosthetic valve fracture improves the hemodynamic results of valve-in-valve transcatheter aortic valve replacement" *Circulation: Cardiovascular Interventions* 10: 1-6). However, this technique comes with drawbacks due to the valvular insufficiency that occurs because of the BVF, which needs to be immediately addressed. To address the valvular insufficiency developed because of pre-VIV BVF, a common practice is to perform BVF after VIV transcatheter valve replacement. To do so, BVF is performed by inflation of a high-pressure balloon positioned across the newly implanted transcatheter valve during rapid ventricular pacing until the old valve's ring is fractured. This practice may avoid valvular insufficiency due pre-VIV BVF. However, since the new transcatheter valve is now implanted, inflating a high-pressure balloon inside of the new transcatheter valve to fracture the old valve would lead to severe compression of the new valve's delicate leaflets over its enclosing stents. This severe pressure on the valve leaflets over the stent can result in leaflet damage and damage the leaflet surface. These changes may provoke platelet aggregation and activation, which facilitates thrombus formation (Dasi L P, et al. 2017 "On the mechanics of transcatheter aortic valve replacement" *Annals of Biomedical Engineering* 45:310-331), and/or the foci of damage on the leaflets act as nidus for accelerated calcification of the valve and diminished durability.

SUMMARY

Some embodiments relate to a percutaneous heart valve delivery system including a valve delivery catheter coupled with:

a first inflatable balloon positioned at a distal end of the valve delivery catheter, wherein the first inflatable balloon is configured to fracture a previously implanted prosthetic heart valve; and a replacement transcatheter heart valve positioned proximal to the first inflatable balloon, wherein the replacement transcatheter heart valve is configured to be implanted subsequently within the previously implanted, fractured prosthetic heart valve, following fracture of the previously implanted heart valve without withdrawal of the percutaneous heart valve delivery system.

In some examples, the percutaneous heart valve delivery system further includes a handle coupled to the valve delivery catheter, wherein the handle includes an adjustment control connected to the first inflatable balloon, wherein the adjustment control is configured to vary a position of the first inflatable balloon in the valve delivery catheter, wherein the first inflatable balloon can be positioned distal, at the same position or proximal in relation to the replacement transcatheter heart valve.

In some examples, the handle further includes a valve expansion/compression control and a valve release control that is configured to disconnect the replacement transcatheter valve from the valve delivery catheter once the replacement transcatheter heart valve is deployed.

In some examples, the transcatheter heart valve is crimped proximally to the first inflatable balloon.

In some examples the transcatheter heart valve is balloon expandable by the first inflatable balloon.

In some examples, the transcatheter heart valve is self-expandable.

In some examples, the percutaneous heart valve delivery system further includes an intravascular ultrasound (IVUS) imaging system, wherein an ultrasound transducer of the IVUS imaging system is slidably movable with respect to the first inflatable balloon and the replacement transcatheter valve in the delivery device, so that imaging and display of the valve delivery catheter, the first inflatable balloon and the replacement transcatheter can be done to image the surrounding anatomy, the advancing catheter, the first inflatable balloon and the replacement transcatheter valve in real-time during replacement of a heart valve.

Some embodiments relate to a method of implantation of new heart valve within a previously implanted prosthetic heart valve including:

inserting the percutaneous heart valve delivery system according to claim 1 into a subject, wherein the first inflatable balloon is first positioned within the previously implanted prosthetic heart valve, inflating the first inflatable balloon to fracture the previously implanted prosthetic heart valve in situ, and deploying the replacement transcatheter heart valve within the previously implanted prosthetic heart valve.

In some examples, an ultrasound transducer of an IVUS imaging system is slidably moved with respect to the first inflatable balloon and the replacement transcatheter valve to image the surrounding anatomy, the first inflatable balloon and the replacement transcatheter valve in real-time during replacement of the previously implanted prosthetic heart valve.

In some examples, the method is to treat a subject wherein the previously implanted prosthetic valve had become stenotic.

In some examples, the method includes:

moving the first inflatable balloon from the position distal of the replacement transcatheter heart valve, after fracture of the previously implanted prosthetic heart valve, to within the lumen of the replacement transcatheter heart valve, and deploying the replacement transcatheter heart valve by inflating the first inflatable balloon within the replacement transcatheter heart valve.

In some examples, the replacement transcatheter heart valve is deployed by self-expansion.

In some examples, the method percutaneous heart valve delivery system includes a second inflatable balloon configured to expand the replacement transcatheter heart valve.

In some examples, the second inflatable balloon is located in a fixed position relative to the replacement transcatheter heart valve, wherein the second inflatable balloon is dedicated to expansion/deployment of the replacement transcatheter heart valve.

Some embodiments relate to a method of implanting a heart valve within a previously implanted prosthetic heart valve including:

inserting the percutaneous heart valve delivery system according to claim 13 into a subject, wherein the first inflatable balloon is first positioned within the previously implanted prosthetic heart valve, inflating the first inflatable balloon to fracture the previously implanted prosthetic heart valve in situ, and inflating the second inflatable balloon within the replacement transcatheter heart valve to expand and deploy the replacement transcatheter heart valve within the now fractured previously implanted prosthetic heart valve.

In some examples, the second inflatable balloon is located in a fixed position relative to the replacement transcatheter heart valve, wherein the second inflatable balloon is dedicated to expansion of the replacement transcatheter heart valve.

Some embodiments relate to a method of valvuloplasty of a native heart valve including:

inserting the percutaneous heart valve delivery system according to claim 1 into a subject, wherein the first inflatable balloon is first positioned within the stenotic native heart valve;

inflating the first inflatable balloon to prime the native heart valve in situ, and deploying the replacement transcatheter heart valve immediately within the native heart valve.

In some examples, the method includes:

moving the first inflatable balloon from the distal position relative to the replacement transcatheter heart valve to within the lumen of the replacement transcatheter heart valve, and inflating the first inflatable balloon to expand the replacement transcatheter heart valve.

In some examples, the replacement transcatheter heart valve is deployed by self-expansion.

In some examples, the replacement transcatheter heart valve is deployed by a second inflatable balloon located in a fixed position relative to the replacement transcatheter heart valve, wherein the second inflatable balloon is dedicated to expansion of the replacement transcatheter heart valve.

DETAILED DESCRIPTION

To mitigate the problems discussed above, we developed a novel percutaneous heart valve delivery system for delivery and implantation of a prosthetic valve that incorporates a balloon. The position of the balloon may be adjustable, and the balloon is used to fracture a previously-implanted prosthetic valve in situ immediately before a new transcatheter valve is implanted, without interfering with the transcatheter valve to be implanted.

Compared to previous transcatheter delivery systems that require a two-step procedure for replacing a previously implanted prosthetic heart valve in a subject, including the use of (1) a first transcatheter system with a balloon that is used to fracture a previously implanted prosthetic heart valve, followed by withdrawal of the first transcatheter balloon from the subject; and (2) a second transcatheter system that is used to deliver a replacement transcatheter heart valve to the subject, we disclose herein delivery systems that mediate both fracture of the previously implanted prosthetic heart valve and replacement with a replacement transcatheter heart valve, without any intermediate withdrawal step following fracture of the previously implanted heart valve. By using a single transcatheter fracture and delivery system and omitting the intermediate withdrawal step required by previous transcatheter systems, the heart valve replacement procedure can be completed efficiently and minimizes undesirable regurgitation through the fractured, previously implanted heart valve prior to replacement with the new prosthetic heart valve.

Figure 1:
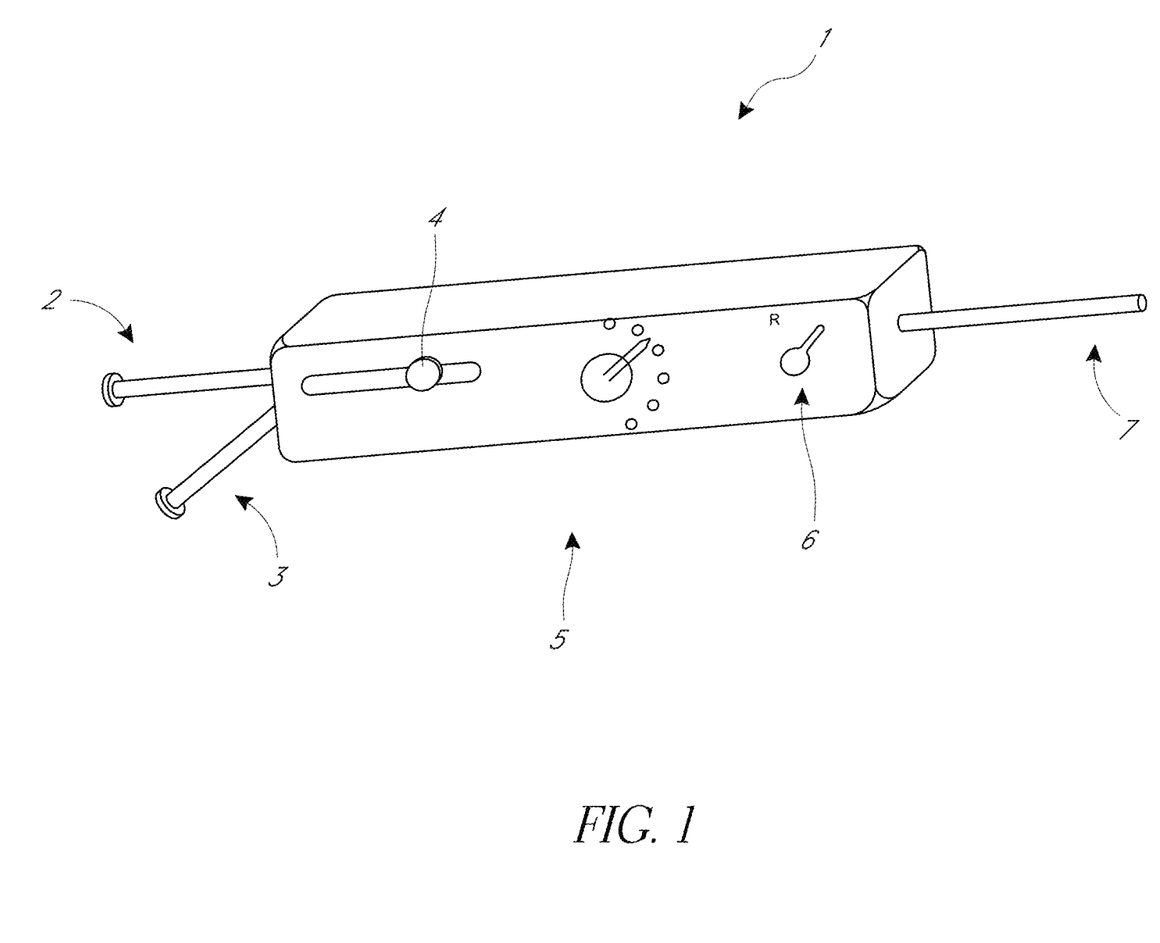
FIG. 1. Handle (1) with balloon inflation/deflation port (2), guide wire port (3), balloon position control (4), valve expansion/compression control dial (5), valve release lever (6) and a catheter (7).
Figure 2:
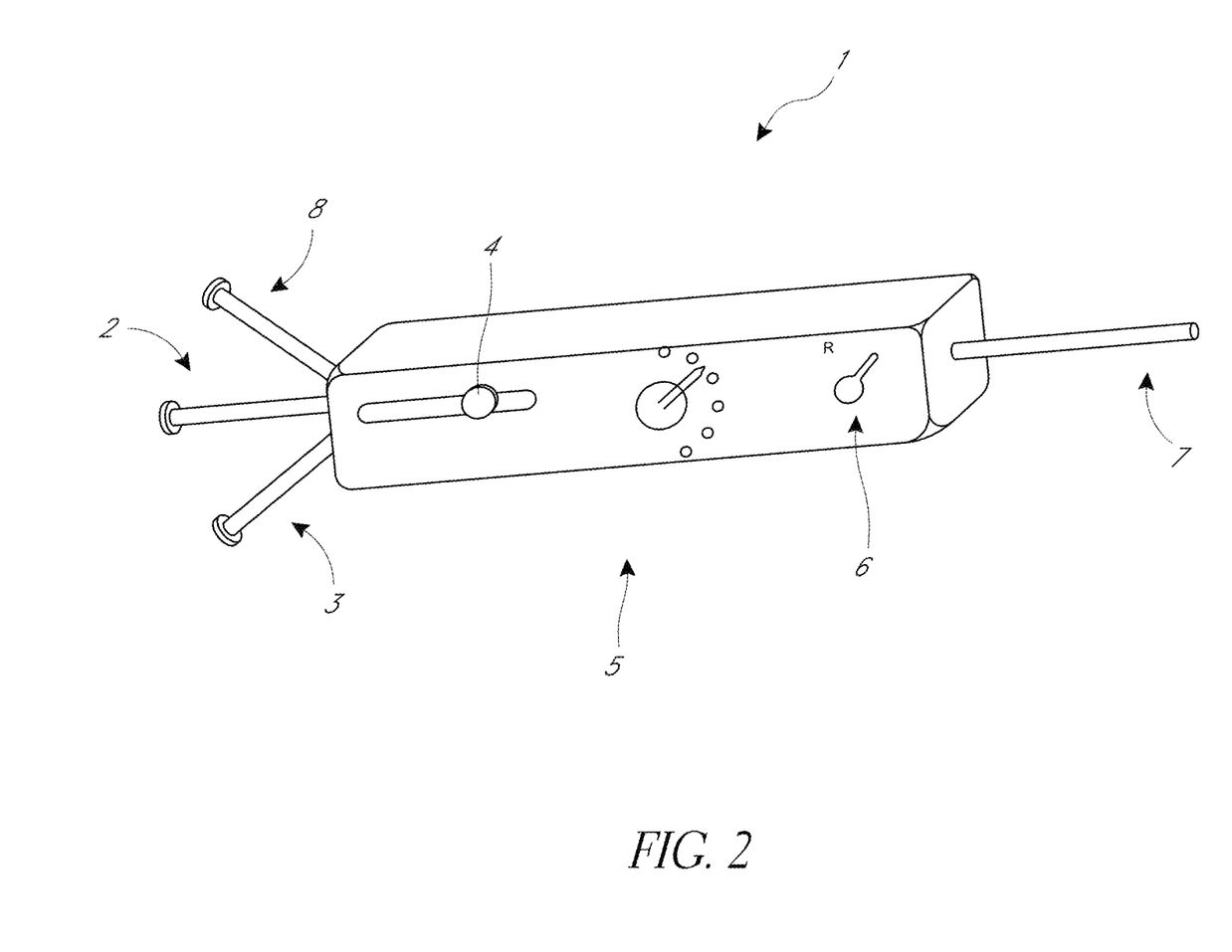
FIG. 2. Handle (1) with first balloon inflation/deflation port (2), second balloon inflation/deflation port (8), guide wire port (3), balloon position controls (4), valve expansion/compression control dial (5), valve release lever (6) and a catheter (7).

The valve delivery systems (e.g., mitral, tricuspid and atrioventricular valves) may be used in connection with a handle that enables remote positioning and inflation or deflation of balloon(s) and release of a prosthetic heart valve. FIG. 1 depicts a handle (1) that includes a guide wire port (3), wherein a guide wire passes through the handle and into a catheter (7). A balloon inflation port (2) enables a distally located balloon to be inflated/deflated. A balloon position control (4) permits a variably positioned balloon to be slid along the catheter. A valve expansion/compression control (5) allows a user to maintain a prosthetic heart valve in a collapsed configuration or to expand and deploy the prosthetic heart valve once in position. A valve release control (6) enables the user to release the prosthetic heart valve from the catheter once it is deployed. The handle shown in FIG. 2 has a second balloon inflation/deflation port (8). Together, the first and second balloon inflation/deflation ports enable two balloons to be independently inflated or deflated.

Balloon-Mediated Expansion/Deployment of Transcatheter Heart Valve

The delivery systems disclosed herein mediate both: (a) fracture of a previously implanted prosthetic heart valve or priming of a native heart valve, and (b) replacement or the previously implanted prosthetic heart valve with another replacement transcatheter heart valve or installation of a prosthetic heart valve in place of the native heart valve.

Figure 3A:
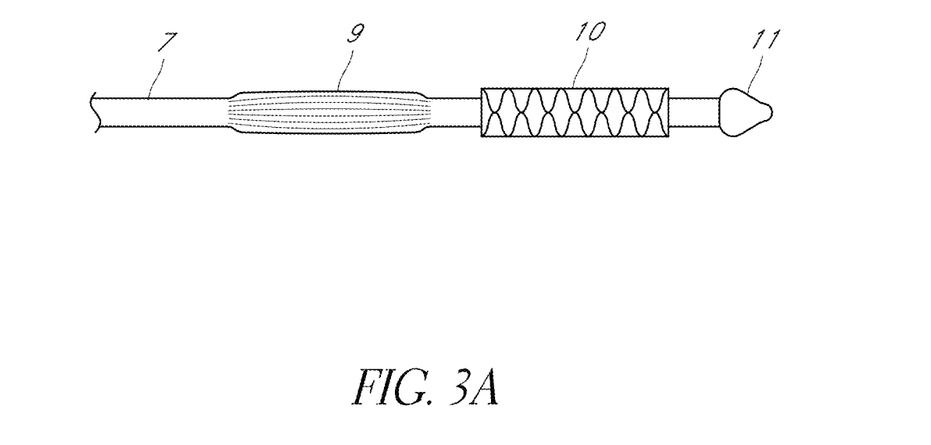
FIG. 3A. Atrioventricular valve delivery system. Balloon deflated, fixed position proximal of the valve.
Figure 3B:
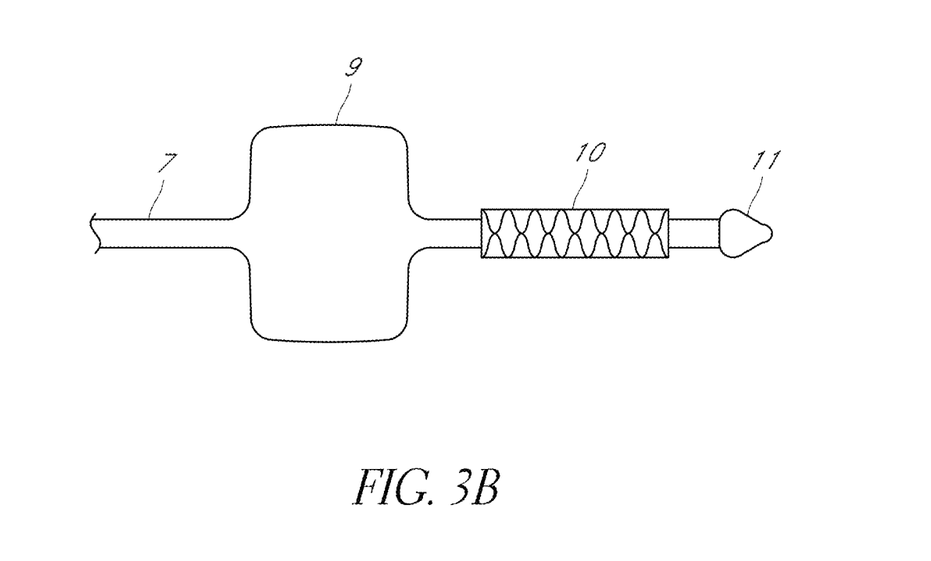
FIG. 3B Atrioventricular valve delivery system. Balloon inflated, fixed position proximal of the valve.
Figure 3C:
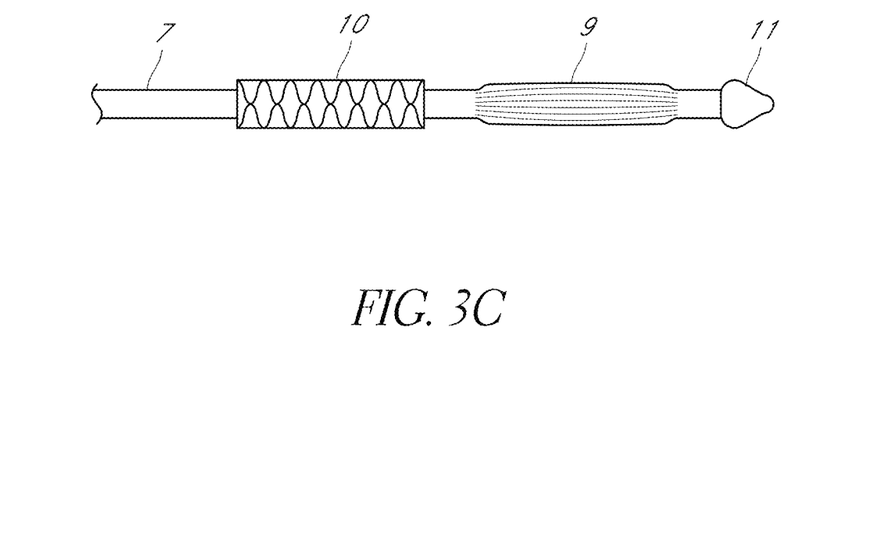
FIG. 3C Atrioventricular valve delivery system. Balloon deflated, fixed position distal of the valve.
Figure 3D:
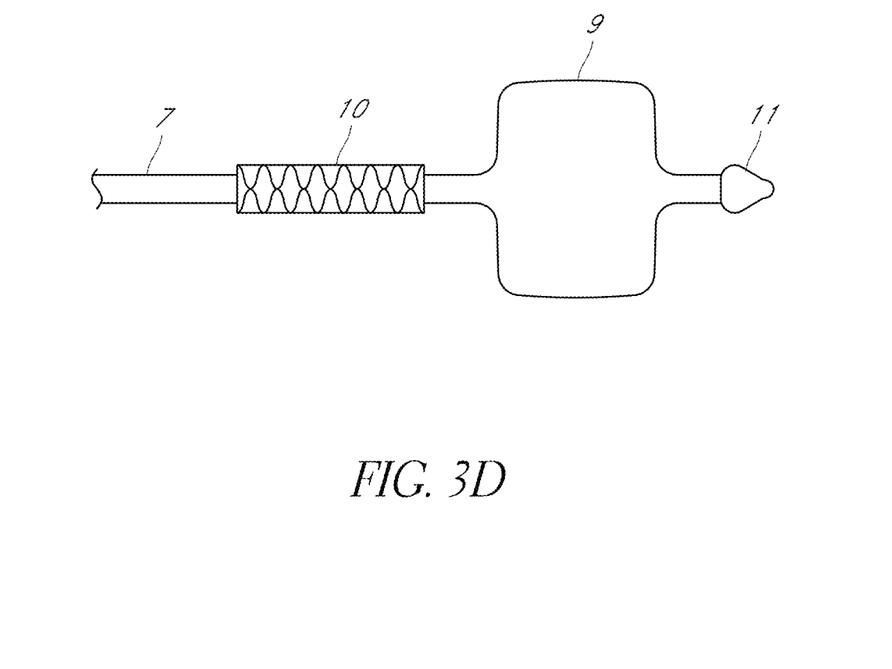
FIG. 3D Atrioventricular valve delivery system. Balloon inflated, fixed position distal of the valve.

FIGS. 3A-3D depict a balloon (9) that is variably positioned in the delivery system relative to the transcatheter heart valve. FIG. 3A shows the deflated balloon (9) positioned on catheter (7) proximal to the transcatheter heart valve (10) and catheter tip (11). FIG. 3B shows balloon (9) inflated, located proximal to the transcatheter heart valve (10) and catheter tip (11). FIG. 3C depicts deflated balloon (9), positioned distally relative to the transcatheter heart valve (10) and catheter tip (11). FIG. 3D shows balloon (9) inflated, positioned distally relative to the transcatheter heart valve (10) and catheter tip (11). By using the balloon position control (4), the balloon is variably positioned relative to the transcatheter heart valve.

Figure 4A:
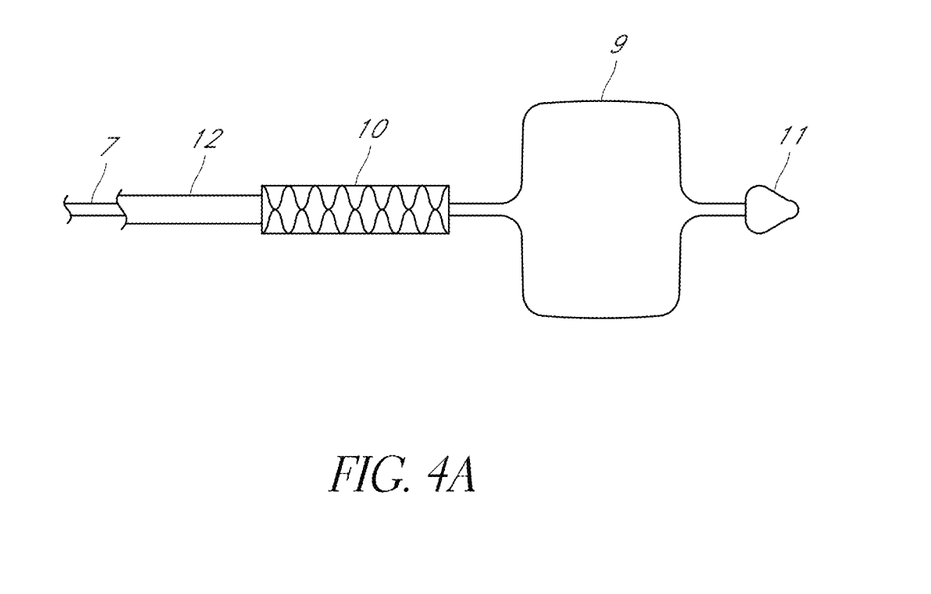
FIG. 4A. Atrioventricular valve delivery system. Balloon inflated, variable position distal of the valve.
Figure 4B:
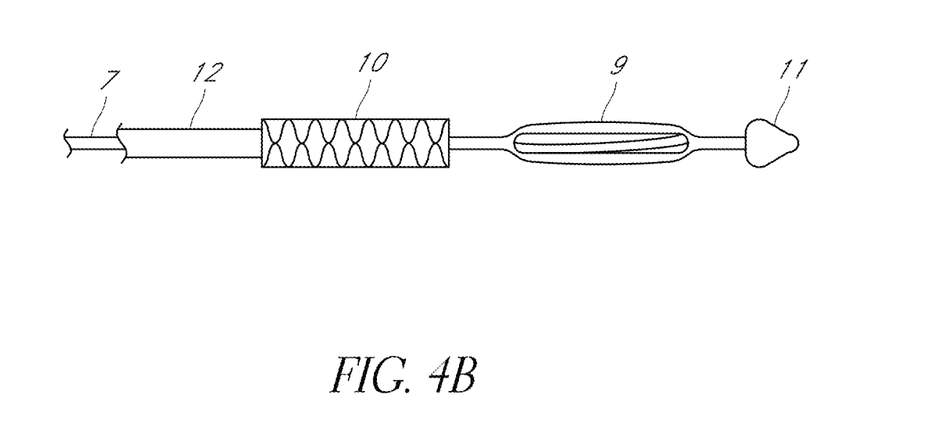
FIG. 4B Atrioventricular valve delivery system. Balloon deflated, variable position distal of the valve.
Figure 4C:
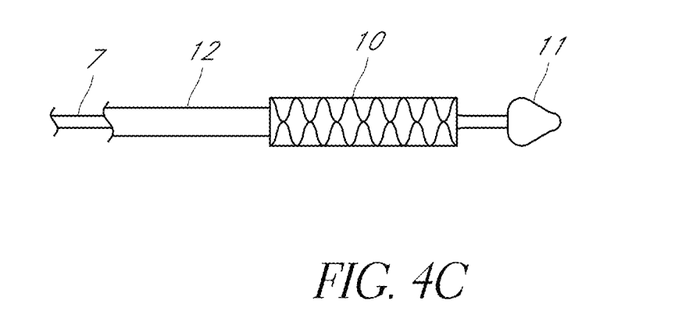
FIG. 4C Atrioventricular valve delivery system. Balloon deflated, variable position within the lumen of the valve.
Figure 4D:
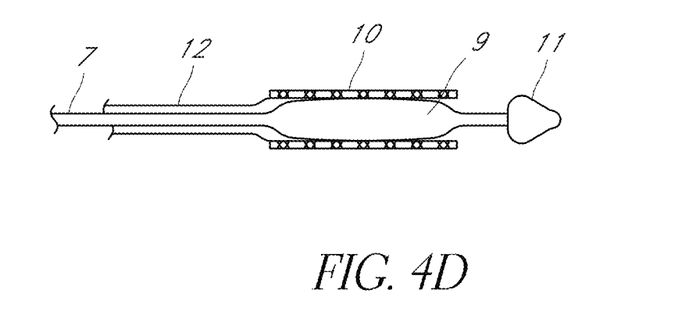
FIG. 4D Atrioventricular valve delivery system. Section view; balloon slightly inflated, variable position within the lumen of the valve.
Figure 4E:
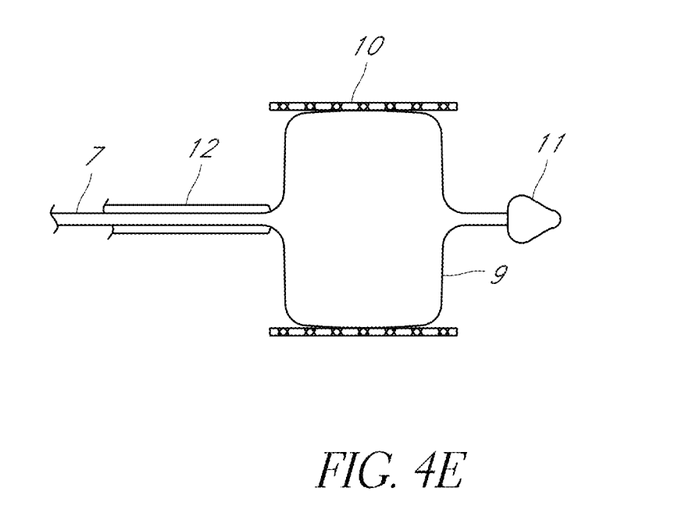
FIG. 4E Atrioventricular valve delivery system. Section view; Balloon fully inflated and valve expanded, variable position within the lumen of the valve.
Figure 5A:
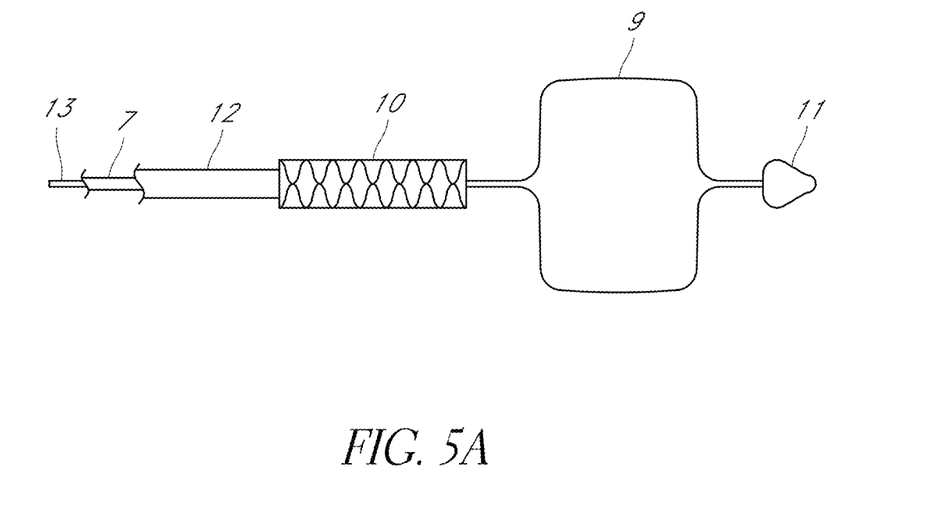
FIG. 5A. Atrioventricular valve delivery system. First balloon inflated, fixed position distal of the valve.
Figure 5B:
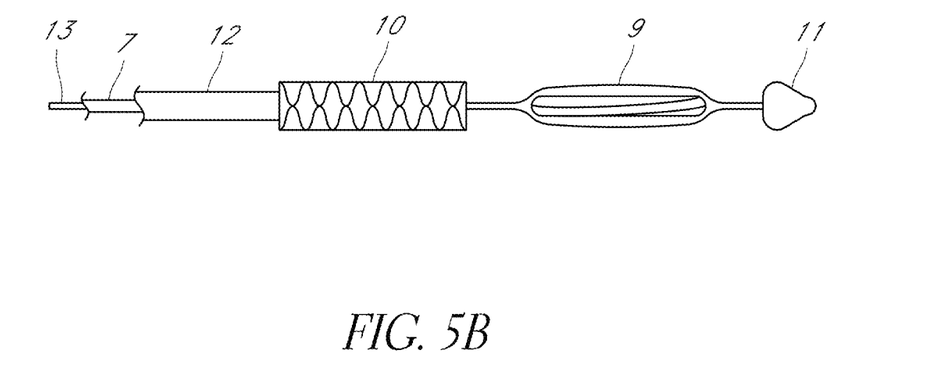
FIG. 5B. First balloon deflated, fixed position distal of the valve.
Figure 5C:
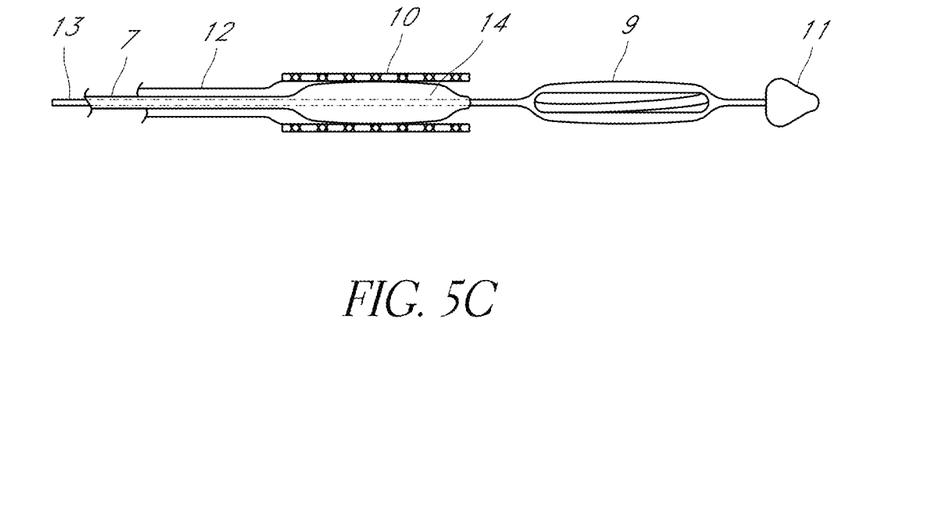
FIG. 5C. Section view: First balloon deflated, fixed position distal of the valve, and second balloon slightly inflated, fixed position within the lumen of the valve.
Figure 5D:
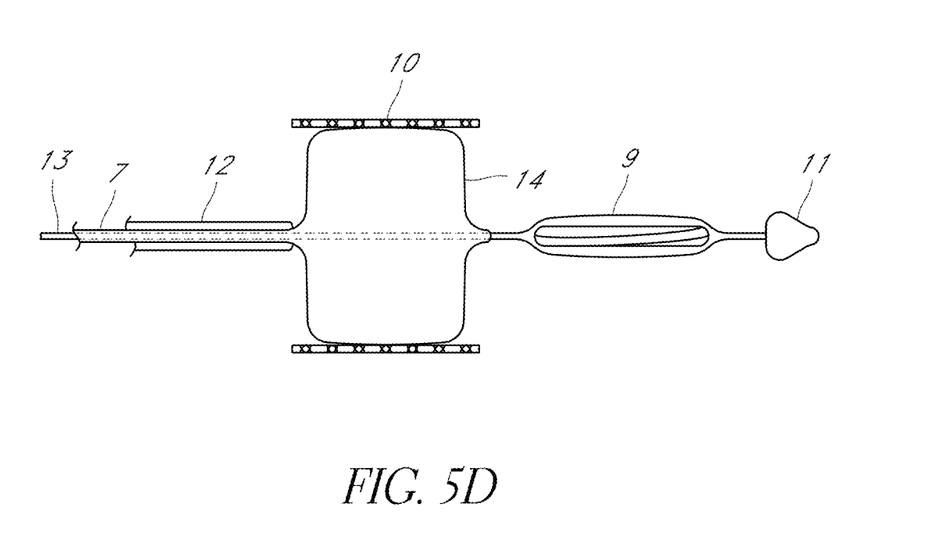
FIG. 5D. Section view: First balloon deflated, fixed position distal of the valve, and second balloon fully inflated, fixed position within the lumen of the valve.
Figures 6A, 6B, 6C, 6D, 6E, 6F:
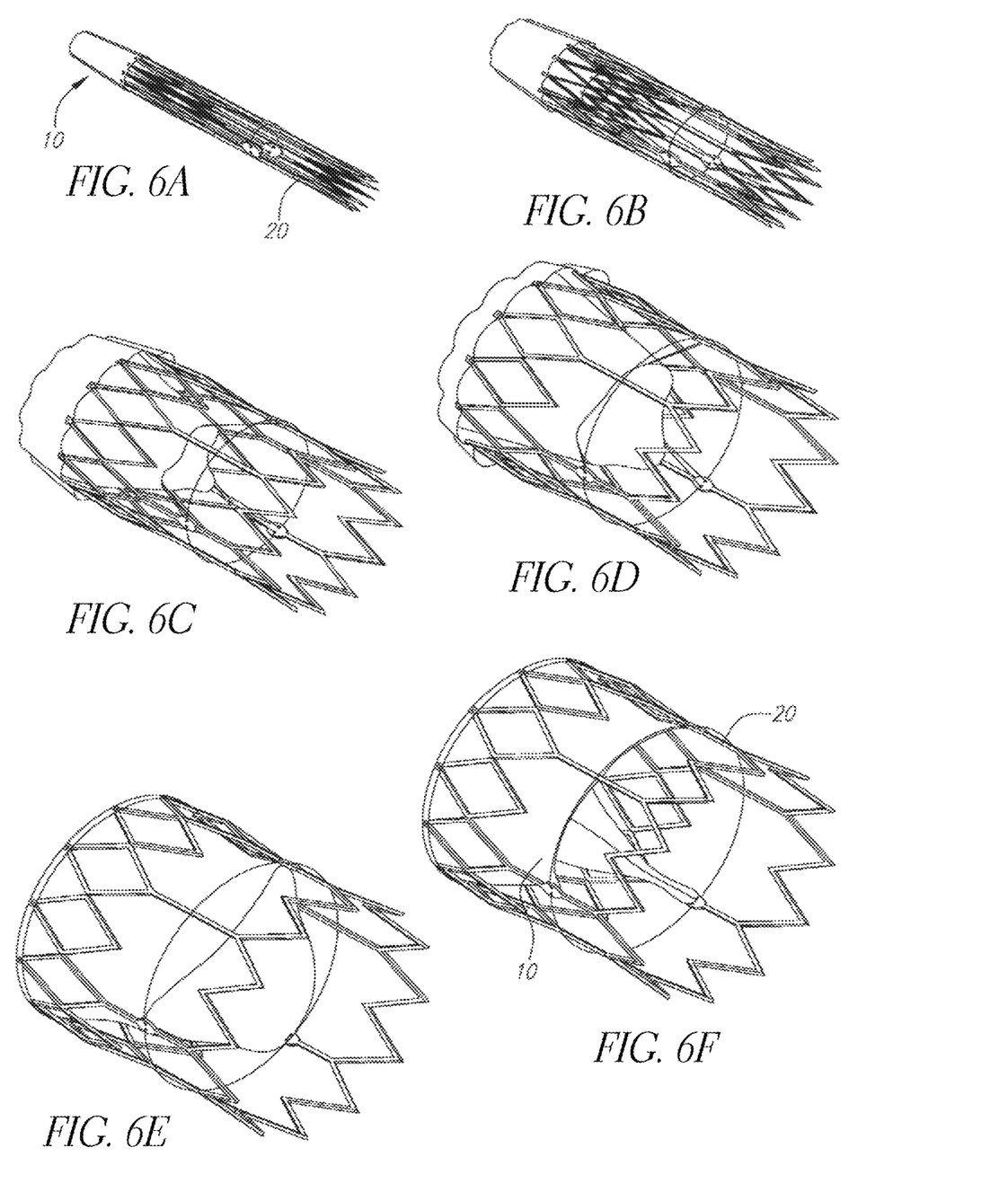
FIG. 6A-6F. Perspective views illustrating an example embodiment of a stent frame and valve in various stages of deployment.

FIG. 4A-4E demonstrates how the variably positioned balloon of FIGS. 3A-3D can be used to first fracture a previously implanted prosthetic heart valve or prime of a native heart valve, at a position distal to a replacement transcatheter heart valve, and then be retracted proximally to within a lumen of the replacement transcatheter heart valve to mediate its expansion/deployment. As show in FIG. 4A, the balloon (9) is positioned distally on catheter (7) relative to the replacement transcatheter heart valve (10) and valve shaft (12) and inflated to fracture the previously implanted prosthetic heart valve or to prime a native heart valve. The balloon (9) is then deflated as shown in FIG. 4B. Retraction of the deflated balloon (9) to within the lumen of the replacement transcatheter heart valve (10) is shown in FIG. 4C. Partial and complete expansion of the replacement transcatheter heart valve (10) by balloon (9) are shown in FIG. 5D and FIG. 5E, respectively.

FIGS. 5A-5D depict a delivery system that includes two balloons that are in fixed positions relative to a transcatheter heart valve (10). A first balloon (9) is used to either fracture a previously implanted prosthetic heart valve or to prime a native heart valve. A second balloon (14) is positioned within a lumen of the replacement transcatheter heart valve (10), where it is positioned to expand the replacement transcatheter heart valve once in position. The first balloon (9) is inflated/deflated by the first balloon inflation/deflation port (2) located on handle (1) that is in communication with the first balloon via first balloon inflation/deflation tube (13) that passes through catheter (7) and optionally through second balloon (14). The second balloon (14) is inflated/deflated by the second balloon inflation/deflation port (8) located on handle (1) that is in communication with the second balloon through catheter (7).

Automatic or Draw Line-Mediated Expansion/Deployment of Transcatheter Heart Valve A single balloon used to either fracture a previously implanted prosthetic heart valve or to prime a native heart for heart valve replacement may be used in combination with an automatically-deployable, spring-loaded transcatheter valve or with a transcatheter valve equipped with arms that are controllable with draw lines, for example as disclosed in U.S. Application Publication No. 2014/0277414 by Kheradvar, et al., incorporated by reference herein in its entirety for all purposes. In this type of embodiment, the transcatheter valve is not expanded using a balloon. Ultrasonic-guided delivery systems are also disclosed in U.S. Application Publication No. 2019/0015203 by Kheradvar et al., incorporated by reference herein in its entirety for all purposes. The balloon may be either in a fixed location distal to the transcatheter valve on the catheter, or it may be variably positioned such that the balloon may be located proximally or distally to the transcatheter valve by passing the balloon through a center of the transcatheter valve.

In one embodiment, the delivery apparatus includes a number of arms (such as, but not limited to three) embedded within its body that hold the valve's stent during the delivery procedure when it is in the collapsed state. The arms may be equipped with adjustable springs that are remotely controllable by the operator and allow for robust radial expansion or deployment of the collapsed stent in increments.

FIGS. 6A-6F illustrate transcatheter valve 10 for delivery in coordinated use with an expandable stent frame 20. Examples regarding valve construction and/or its manipulation for delivery are disclosed in U.S. Pat. No. 8,133,270 to Kheradvar, et al., incorporated by reference herein in its entirety for all purposes.

In use, the arms remain attached to the valve stent frame until the stent frame is fully deployed. If the stent/stent frame is not properly deployed, the arms, which are still releasably attached to the stent until intended release, can be used for partial contraction of the stent for repositioning purposes. When the stented valve is properly positioned as desired within the aortic annulus, the arms will be released from the stent, and return to their embedded/retracted positions within the apparatus. Then the entire apparatus is retracted. It may be retracted from the heart or vasculature over any guide wire used and/or through any delivery catheter employed for site access.

In another system embodiment allowing for stented valve delivery, repositioning, and/or percutaneous retrieval, draw line filaments are positioned through the distal end of a pusher sleeve (or draw tube), along a lumen of the sleeve (or tube), out through holes in the sleeve (or tube), out through proximal frame holes, along the surface of a heart valve frame, in through distal frame holes, in through the distal end of the sleeve (or tube), along the lumen of the sleeve (or tube), and out the proximal end of the sleeve (or tube). Variations on this approach are possible as are various optional features of the stent frame facilitating such use.

The draw lines may comprise polyester (PE), polytetrafluoroethylene (PTFE), suture material, or another high strength (preferably a biocompatible fiber) braid or bundle of fibers such as ultra-high-molecular-weight polyethylene (UHMWPE, sometimes shortened to UHMW). In this embodiment and others described herein, the heart valve frame may comprise superelastic NiTi alloy heatset in a desired shape, it may be constructed of a so-called "engineering plastic" such as polyetheretherketone (PEEK) or may be constructed otherwise. Various surface treatments or finishes may be desirable. In the case of a NiTi (Nitinol) or another metallic material implant, an electro-polished surface may be preferred.

Collapsed and expanded states of a heart valve can be controlled by varying the position and/or tension applied to the draw lines. A customized handle may be provided as a user interface. Draw line tension can be increased until the heart valve frame is fully collapsed and fully releasing the draw line tension allows the self-expanding heart valve frame to fully expand. The heart valve frame may be put in an intermediate state by varying the tension applied to the draw lines. Moreover, the system can be setup to allow a range of lateral control of the stent position during delivery. In one variation, a "joystick" control interface is provided; in another a model of the implant (or at least the stent frame portion of the valve to be delivered) is used. In one embodiment, a gimbal handle may be used in connection with a delivery system disclosed herein, for example as described in U.S. application Ser. No. 16/866,913 by Kheradvar et al., incorporated by reference herein in its entirety.

In yet another delivery system embodiment allowing for delivery, repositioning, and/or percutaneous retrieval, different means or entities are provided to control the state of device deployment (variably, from fully collapsed to fully expanded) of the proximal end of a self-expanding heart valve device. Such means or entities pertain to the use of multiple sleeve or sheath features (herein optimally referred to as "zip tube" parts or an assembly with "zip tube" sheaths or fingers) provided to mechanically change an angle between adjacent strut elements and thereby the proximity of the struts. In use, the zip tube sheaths (or fingers) collapse the heart valve frame by "zipping" the struts into closer proximity.

In this embodiment, the ends of a self-expanding heart valve frame are configured with a link feature. A self-expanding retainer is constructed and configured with diametrically collapsible retainer arms or fingers. A zip tube part or assembly with diametrically expandable/collapsible sheath fingers is configured in such a manner to allow the zip tube fingers to slide over the retainer fingers. The ends of the retainer fingers are configured with a clasp or link feature so as to mate to the heart valve frame clasp or link features.

The zip tube assembly may be partially advanced (distally) to trap the heart valve frame and retainer such that they will not unlink because the inner diameter (or inner dimension(s)) of the zip tube fingers are constructed so as to constrain the linked heart valve frame and retainer from unlinking when positioned around the linked frame or retainer. With the retainer serving as a means to secure the valve in position, the zip tube assembly may be variably advanced (relative to the linked heart valve frame or retainer) to variably (e.g., partially) collapse the proximal end of the heart valve device or fully advanced to fully collapse the proximal end of the heart valve device.

The zip tube part assembly may be variably retracted to allow the proximal end of the self-expanding heart valve device to variably (partially) expand or retracted sufficient to allow the self-expanding heart valve device to fully expand. Alternatively, the zip part or assembly may be secured in position and the retainer may be variably retracted to variably collapse the proximal end of the heart valve device up to fully collapsed or variably advanced to allow the self-expanding heart valve device to variably expand up to fully expanded. The zip tube part or assembly can be fully retracted allowing the heart valve frame and retainer to unlink thereby releasing the heart valve device from the delivery system so that the heart valve device may be left in position and the delivery system may be removed.

In addition, any of the subject delivery system architectures may incorporate a visualization system for image-directed heart valve delivery. Alternatively, other features for restraining and/or manipulating a self-expanding stent frame or a ballooned stent frame approach may be employed in an image-guided system. These embodiments involve a catheter or catheter-like device that utilizes an integrated imaging modality with a deployment mechanism. As such, these embodiments may be used to accurately deploy a heart valve into a patient with greater accuracy and precision than with conventional procedural imaging modalities where direct visual confirmation is not possible.

In these embodiments, the delivery system incorporates a catheter-based imaging modality within the device, such as, but not limited to, intravascular ultrasound (IVUS), intravascular photoacoustic (IVPA) imaging, optical coherence tomography (OCT), raman spectroscopy, or an optical method, capable of detecting features of a vessel in which the catheter is inserted. The selected imaging systems allow clinicians to image both the surrounding anatomy and the advancing catheter in real-time during the procedure. Ultrasound-guided delivery systems for accurate positioning or repositioning of transcatheter heart valves are disclosed in U.S. Application Publication No. 2019/0015203 by Kheradvar, et al., incorporated by reference herein in its entirety for all purposes.

In one example, since IVUS is a tomographic imaging modality, a 3D image of the aortic root can be produced through pull-back imaging. High-resolution IVUS is well-known for interrogating the lumen wall of vessels and has also been used to visualize metal stents in vivo. In the example of IVUS hardware, a physician can accurately image and position the implantable valve device without the use of ionizing radiation or nephrotoxic contrast agents. Furthermore, IVUS advantageously provides for a real-time imaging modality.

In some embodiments, the delivery system has a valve delivery catheter with a first lumen, and an ultrasound imaging catheter with a second lumen and an imaging probe at the distal end, wherein the ultrasound imaging catheter is configured to moveably pass over a guide wire passing through the second lumen of the ultrasound imaging catheter.

In some embodiments, a guide wire lumen allows "over-the-wire" use. In some examples, the delivery system is configured to work with a variety of guide wires, but does not include a guide wire per se. This enables versatility in matching the delivery system with any guide wire that best suites a given need, thereby providing a cardiologist flexibility to adjust the selection of guide wire, even during a procedure. There are many different types of guide wires, each having different properties such as length, stiffness, torqueability, having a floppy tip and a stiff body to enable easy tip navigation, pushability, coatings, e.g., with a polymer, such as silicone or polytetrafluoroethylene (PTFE), to increase lubricity, etc. Therefore, the delivery systems disclosed herein allow a physician to combine optimal features of a particular guide wire with the power of an ultrasound imaging catheter/ultrasound imaging probe. This feature provides a significant advantage for a physician in selecting and providing optimal care to a patient.

Imaging modalities, such as IVUS, allow clinicians to image both the surrounding anatomy and the advancing catheter in real-time during the procedure. Since IVUS is a tomographic imaging modality, a 3D image of the aortic root can be produced through pull-back imaging. High-resolution IVUS is well-known for interrogating the lumen wall of vessels and has also been used to visualize metal stents in vivo. The invention can more accurately image and position the TAVR device without the use of ionizing radiation or nephrotoxic contrast agents. Furthermore, IVUS is a real-time imaging modality.

The delivery device can be configured to radially expand the valve for deployment and/or redeployment in the target delivery site. The delivery device can also be configured to radially contract or compress the valve, such as with the use of multiple filaments, to assist in repositioning and/or recapturing the valve. The delivery device can be used in all steps of the delivery process, which can include advancement through the vasculature to a target delivery site (e.g., the aortic root), positioning of the valve with respect to the target delivery site, deployment of the valve (e.g., by radial expansion), recapture of the valve (e.g., by partial are full radial compression), repositioning of the valve with respect to the target delivery site, redeployment of the valve, and/or withdrawal of the device. These steps can be performed as many times as necessary to obtain the desired orientation and placement within the vasculature.

During any and all steps of the delivery process (e.g., advancement, positioning, capture, recapture, repositioning, redeployment, withdrawal, etc.) an intravascular ultrasound (IVUS) imaging device can be used to obtain image data of the target delivery site, the valve, and/or the delivery device. An ultrasound imaging device can include one or more imaging elements (e.g., transducers) coupled with an elongate shaft that are together slidably movable with respect to the delivery device.

One or more imaging elements can emit and/or receive ultrasound signals and produce one or more output signals that are usable to generate images of the target deployment site, the valve, and/or the delivery device. For example, the one or more output signals can be transferred from the one or more imaging elements along the elongate shaft (e.g., by an electrical conductive path) to one or more image processing and/or graphics rendering devices that can render image data suitable for display to a medical professional on a screen or monitor. The imaging and display processes can occur in real time such that minimal delay (e.g., less than one second) between capture of the ultrasound image data and display is perceived by the medical professional. The image processing and/or graphics rendering devices can include one or more processors and one or more non-transitory memories on which is stored one or more instructions for processing the data output from the one or more imaging elements to generate image data suitable for viewing on a display communicatively coupled with the image processing and/or graphics rendering devices.

The images displayed to the medical professional can be two dimensional cross-sectional images (e.g., radial or longitudinal) and/or three-dimensional images (e.g., showing surface contours). In some embodiments, the one or more imaging elements are rotated to capture a 360° radial cross-sectional view, and in other embodiments the one or more imaging elements are positioned with a 360° field of view such that no rotation is needed to capture a 360° radial cross-sectional view. The one or more imaging elements can be moved proximally and/or distally (e.g., a longitudinally) to obtain radial cross-sectional images at various positions along the length of the aortic root. These images taken at various positions can then be combined to render a three-dimensional image of a longitudinal span of the aortic root. In all embodiments, images obtained by the ultrasound imaging device can depict the native valve's general structure, including lumen size, leaflet position and thickness, and location of calcified inclusions to the extent present in the native valve or in a calcified artificial valve already implanted therein.

A catheter system can be based upon an imaging catheter or a valve delivery catheter. In an embodiment where the catheter system is based upon the valve delivery catheter, the imaging modality device can be inserted through the center of the valve delivery catheter, where the active imaging element is aligned with a feature of the valve delivery catheter, such as, but not limited to the catheter tip, the distal or proximal end of the valve stent, or some other predetermined landmark of the valve delivery catheter. Positioning of the imaging device on the circumference of the valve delivery catheter is also possible in another embodiment to prevent visual hindrance from the implanted stent.

In yet another embodiment, the valve delivery system is based upon the imaging catheter, and the deployment mechanism is inserted through the lumen of the imaging catheter, such as, but not limited to, through a guidewire port of the imaging catheter. Furthermore, the delivery system referred herein is not limited to the delivery of a heart valve device, but could be used to deliver therapy to a localized region through the use of a catheter. Such examples of delivery could include, but are not limited to, delivery of drugs or other therapeutic agents, delivery of RF irradiation, or delivery of another device.

Operation of the delivery system allows visualization of the surrounding anatomy during insertion of the imaging catheter in the context of the location of the delivery catheter. As such, the location of the delivery catheter relative to the surrounding environment may always be known. In one embodiment, the delivery system is fixed relative to the imaging transducer within the catheter. In another embodiment, the two components can be moved relative to one another. However, in embodiments where relative motion is allowed, the relative motion is advantageously tracked or known in order to maintain accuracy in the advancing catheter.

The subject delivery devices, kits in which they are included (with and without valve installation or assembly), methods of use and manufacture (such as assembly of the delivery system and frame alone and/or with included valve) are all included within the scope of the present disclosure.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A valve-in-valve delivery system comprising a valve delivery catheter coupled with:
   a first inflatable balloon variably positioned in the valve delivery catheter, wherein the first inflatable balloon is configured to fracture a previously implanted prosthetic heart valve; and
   a replacement transcatheter heart valve positioned either proximally or distally to the first inflatable balloon, wherein the replacement transcatheter heart valve is configured to be implanted subsequently within the previously fractured implanted prosthetic heart valve, without withdrawal of the valve delivery system;
   a handle coupled to the valve delivery catheter, wherein the handle comprises an adjustment control for the first inflatable balloon and the replacement transcatheter heart valve.

2. The valve-in-valve delivery system according to claim 1, wherein the adjustment control is configured to vary a position of the first inflatable balloon in the valve delivery catheter, wherein the first inflatable balloon can be positioned distal, at the same position or proximal in relation to the replacement transcatheter heart valve.

3. A percutaneous heart valve delivery system comprising a valve delivery catheter coupled with:
   a first inflatable balloon positioned at a distal end of the valve delivery catheter, wherein the first inflatable balloon is configured to fracture a previously implanted prosthetic heart valve;
   a replacement transcatheter heart valve positioned proximal to the first inflatable balloon, wherein the replacement transcatheter heart valve is configured to be implanted subsequently within the previously implanted, fractured prosthetic heart valve, following fracture of the previously implanted heart valve without withdrawal of the percutaneous heart valve delivery system; and
   a handle coupled to the valve delivery catheter, wherein the handle comprises an adjustment control connected to the first inflatable balloon and the valve, wherein the adjustment control is configured to vary a position of the first inflatable balloon in the valve delivery catheter, wherein the first inflatable balloon can be positioned distal, at the same position or proximal in relation to the replacement transcatheter heart valve, wherein the handle comprises a valve expansion/compression control and a valve release control that is configured to disconnect the replacement transcatheter valve from the valve delivery catheter once the replacement transcatheter heart valve is deployed.

4. The percutaneous valve delivery system according to claim 1, wherein the transcatheter heart valve is crimped proximally to the first inflatable balloon.

5. The percutaneous heart valve delivery system according to claim 1, wherein the transcatheter heart valve is balloon expandable by the first inflatable balloon.

6. The percutaneous heart valve delivery system according to claim 1, wherein the transcatheter heart valve is self-expandable.

7. The percutaneous heart valve delivery system according to claim 3, further comprising an intravascular ultrasound (IVUS) imaging system, wherein an ultrasound transducer of the IVUS imaging system is slidably movable with respect to the first inflatable balloon and the replacement transcatheter valve in the delivery device, so that imaging and display of the valve delivery catheter, the first inflatable balloon and the replacement transcatheter can be done to image the surrounding anatomy, the advancing catheter, the first inflatable balloon and the replacement transcatheter valve in real-time during replacement of a heart valve.

8. A method of implantation of new heart valve within a previously implanted prosthetic heart valve comprising:
   inserting the percutaneous heart valve delivery system according to claim 1 into a subject, wherein the first inflatable balloon is first positioned within the previously implanted prosthetic heart valve,
   inflating the first inflatable balloon to fracture the previously implanted prosthetic heart valve in situ, and
   deploying the replacement transcatheter heart valve within the previously implanted prosthetic heart valve.

9. A method of implantation of new heart valve within a previously implanted prosthetic heart valve comprising:
   inserting the percutaneous heart valve delivery system according to claim 3 into a subject, wherein the first inflatable balloon is first positioned within the previously implanted prosthetic heart valve,
   inflating the first inflatable balloon to fracture the previously implanted prosthetic heart valve in situ, and
   deploying the replacement transcatheter heart valve within the previously implanted prosthetic heart valve, wherein an ultrasound transducer of an IVUS imaging system is slidably moved with respect to the first inflatable balloon and the replacement transcatheter valve to image the surrounding anatomy, the first inflatable balloon and the replacement transcatheter valve in real-time during replacement of the previously implanted prosthetic heart valve.

10. The method according to claim 8 to treat a subject wherein the previously implanted prosthetic valve had become stenotic.

11. A method of implantation of new heart valve within a previously implanted prosthetic heart valve comprising:
inserting the percutaneous heart valve delivery system according to claim 3 into a subject, wherein the first inflatable balloon is first positioned within the previously implanted prosthetic heart valve,
inflating the first inflatable balloon to fracture the previously implanted prosthetic heart valve in situ,
deploying the replacement transcatheter heart valve within the previously implanted prosthetic heart valve
moving the first inflatable balloon from the position distal of the replacement transcatheter heart valve, after fracture of the previously implanted prosthetic heart valve, to within the lumen of the replacement transcatheter heart valve, and
deploying the replacement transcatheter heart valve by inflating the first inflatable balloon within the replacement transcatheter heart valve.

12. The method of claim 8, wherein the replacement transcatheter heart valve is deployed by self-expansion.

13. The percutaneous heart valve delivery system according to claim 3, further comprising a second inflatable balloon configured to expand the replacement transcatheter heart valve.

14. The percutaneous heart valve delivery system according to claim 13, wherein the second inflatable balloon is located in a fixed position relative to the replacement transcatheter heart valve, wherein the second inflatable balloon is dedicated to expansion/deployment of the replacement transcatheter heart valve.

15. A method of implanting a heart valve within a previously implanted prosthetic heart valve comprising:
inserting the percutaneous heart valve delivery system according to claim 13 into a subject, wherein the first inflatable balloon is first positioned within the previously implanted prosthetic heart valve,
inflating the first inflatable balloon to fracture the previously implanted prosthetic heart valve in situ, and
inflating the second inflatable balloon within the replacement transcatheter heart valve to expand and deploy the replacement transcatheter heart valve within the now fractured previously implanted prosthetic heart valve.

16. The method of claim 14, wherein the second inflatable balloon is located in a fixed position relative to the replacement transcatheter heart valve, wherein the second inflatable balloon is dedicated to expansion of the replacement transcatheter heart valve.

17. A method of valvuloplasty of a native heart valve comprising:
inserting the percutaneous heart valve delivery system according to claim 3 into a subject, wherein the first inflatable balloon is first positioned within the stenotic native heart valve;
inflating the first inflatable balloon to prime the native heart valve in situ, and
deploying the replacement transcatheter heart valve immediately within the native heart valve.

18. The method according to claim 17 comprising:
moving the first inflatable balloon from the distal position relative to the replacement transcatheter heart valve to within the lumen of the replacement transcatheter heart valve, and
inflating the first inflatable balloon to expand the replacement transcatheter heart valve.

19. The method according to claim 17, wherein the replacement transcatheter heart valve is deployed by self-expansion.

20. The method of claim 17, wherein the replacement transcatheter heart valve is deployed by a second inflatable balloon located in a fixed position relative to the replacement transcatheter heart valve, wherein the second inflatable balloon is dedicated to expansion of the replacement transcatheter heart valve.

* * * * *